United States Patent [19]

Louderback

[11] Patent Number: 4,978,688
[45] Date of Patent: Dec. 18, 1990

[54] METHOD OF TREATING WHITE BLOOD CELLS

[76] Inventor: Allan L. Louderback, 9661 Longden Ave., Temple City, Calif. 91780

[21] Appl. No.: 328,322

[22] Filed: Mar. 24, 1989

[51] Int. Cl.$^5$ .................... A01N 31/14; A61K 31/075
[52] U.S. Cl. .................................................. 514/722
[58] Field of Search ........................................ 514/722

[56] References Cited

U.S. PATENT DOCUMENTS

| 4,250,051 | 2/1981 | Armstrong | 252/408 |
| 4,465,774 | 8/1984 | Huang et al. | 465/15 |
| 4,789,545 | 12/1988 | Woods et al. | 514/802 |

OTHER PUBLICATIONS

McCutcheon's Emulsifiers & Detergents 1987, p. 99.
Schick, Nonionic Surfactants, pp. 86,87,126, Marcel Dekker.
Merck Index, 10th. ed., p. 1094.

Primary Examiner—Mukund J. Shah
Assistant Examiner—C. L. Cseh

[57] ABSTRACT

A method of removing virus from white blood cells without causing concurrent damage to any red blood cells is provided by treating the white blood cells with an effective amount of a special detergent which selectively lyses the white blood cells without causing substantial lysis of any red blood cells in admixture therewith.

7 Claims, No Drawings

METHOD OF TREATING WHITE BLOOD CELLS

BACKGROUND OF THE INVENTION

This invention relates to a method of removing virus from white blood cells without causing concurrent damage to the red blood cells in admixture therewith.

In recent years, considerable effort has been undertaken by scientists and blood bank specialists to free the nation's blood supply from contamination by viruses, especially the hepatitis viruses. With the recent discovery and identification of the virus reported to cause acquired immune deficiency syndrome (AIDS), an additional contamination problem has appeared with respect to the blood supply. This contamination can arise through collection of blood from donors carrying the AIDS virus, also known as human immuno-deficiency virus (HIV).

While suggestions have been made for individuals to avoid the potential problem of blood contamination with the AIDS virus by making autologous blood donations, such approaches are not likely to be practical except for storing relatively small amounts of blood for scheduled operations.

In U.S. Pat. No. 4,833,165, a method is described for inactivating the AIDS virus in blood or a blood component by treatment with an effective amount of about 0.1 to 5% of phenol, formaldehyde or mixtures thereof and then washing the residual chemical agent from the treated blood or blood component. This method is especially adapted for treatment of the red blood cells. In instances where the red blood cells are not completely separated from the white blood cells, some residual virus may still be present in the latter cells.

Accordingly, a method for removing virus from white blood cells without causing concurrent damage to the red blood cells would have significant utility.

DESCRIPTION OF THE INVENTION

In accordance with the present invention a method is provided for removing intracellular virus from white blood cells without causing concurrent damage to any red blood cells in admixture therewith. The method comprises treating the white blood cells with an effective amount of a special detergent which selectively lyses the white blood cells without causing lyses of any red blood cells in admixture therewith to thereby release the white blood cell-containing virus into the cell medium or cell lysate.

After this lysing treatment, the virus is then preferably inactivated or removed from the red blood cell milieu by treatment with an effective amount of from about 0.1% to about 5% of phenol, formaldehyde or mixture thereof followed by washing the residual chemical agent therefrom as described in U.S. Pat. No. 4,833,165, the disclosure of which is incorporated herein by reference.

It has been found unexpectedly that certain detergents are capable of selectively lysing the white blood cells without concurrently lysing the red blood cells. This is believed to be a unique discovery when it is considered that detergents used heretofore for lysing blood cells will lyse the red cells and leave the white cell s intact so that they can be counted. Examples of such detergents used heretofore are sodium lauryl sulfate, Triton ® X-100, Tween ® 80, diethylphthalate, cetyltrimethylammonium bromide (hexadecyltrimethyl-ammonium bromide or Cetrimide), alkyltrimethylammonium bromide (C16 or Bromat), myristyltrimethylammonium bromide (Mytab) and the like detergents, as well as the natural plant material, saponin. The use of such detergents for lysing blood cells for application in calibrating and control solutions for blood analysis and hemoglobin determinations is illustrated, for example, in U.S. Pat. Nos. 4,250,051 and 4,465,774.

The preferred detergents for use in the present invention are the so-called polyoxyethylene alcohols, also referred to as polyethylene glycol fatty alcohol ethers, which contain from about 20 to 23 oxyethylene groups in the molecule and are derivatives of $C_{12}$–$C_{18}$ fatty alcohols. Illustrative examples of these useful detergents are polyoxeyethylene (23) lauryl ether (Brij 35),
polyoxyethylene (20) cetyl ether (Brij 58), and
polyoxyethylene (20) stearyl ether (Brij 78).

By way of comparison, polyoxyethylene alcohols having substantially fewer oxyethylene groups in the molecule are not useful since they also lyse the red blood cells. Examples of such detergents are polyoxyethylene (4) lauryl ether (Brij 30);
polyoxyethylene (10) oleyl ether (Brij 96).

The amount of the special detergent used in the method of the invention can widely range from about 0.2% to about 50% by volume of the blood sample or other treatment milieu containing the white blood cells in admixture with the red blood cells. The preferred level of active detergent is about 1–2% by volume of the white blood cell mixture. By way of example, a commercially available 30% solution of the detergent when used at a concentration of 5% by volume of the treated mixture will provide 1.5% of the active detergent.

The detergent treatment of the white blood cells can be carried out at ambient temperature or within a range of from about 2° C. to about 45° C.

The detergent can be added directly to the container such as blood bags or tubes in which the blood is initially collected from the patient or in which the blood is stored, as the case may be. To facilitate uniform mixing of the detergent with the blood medium, the bags or tubes may be placed on a gentle rotator or left static for a suitable period of time. However, blood packs are not generally agitated during their useful time period, and, therefore, can remain static during the detergent treatment period herein.

The detergent treatment of the invention thus removes the intracellular and membrane associated virus from the white cells by selective lysis as defined herein. Following this lysis, the virus can be inactivated such as by the preferred chemical treatment described hereinbefore, or by mechanical treatment, for example, by washing the red blood cells in special centrifuge washing systems to remove the cellular material and membranes by washing away with saline or other physiologically acceptable solutions such as ACD, CPD and the like.

The following examples will further illustrate the invention although it will be appreciated that the invention is not limited to these specific examples.

EXAMPLE 1

This example illustrates the use of a 30% solution of Brij 35 at a concentration of 5% to lyse white blood cells without substantially lysing the red blood cells in human whole blood samples collected in either ACD or disodium EDTA anticoagulant solution. The blood samples were collected in ACD tubes to a 6 ml fill containing 300 μl of the Brij 35 and in the disodium EDTA tube to a 5 ml fill containing 250 μl of the Brij 35. The detergent treated samples (Experimental) and untreated samples (Control) were then tested on an automated blood cell counting and analyzing instrument (Coulter Counter) to determine characteristic parameters such as the red blood count (RBC), white blood count (WBC) hematocrit (HCT), hemoglobin (Hgb), mean corpuscular volume (MCH), mean corpuscular hemoglobin concentration (MCHC), platelet (PLT) and the like. Values were recorded after 2, 4, 6 and 24 hours following treatment. The results are set forth in Tables 1 and 2, below. Table 1 records the values in the ACD tubes for the untreated (Control) and detergent treated (Experimental) samples; whereas, Table 2 shows the corresponding values in the EDTA tubes. The results can be summarized as follows:

1. The control white blood counts (WBC) remain relatively constant for the 24 hour period.
2. The experimental white blood counts (WBC) decline with time.
3. The red blood counts (RBC) remain relatively constant in both the control and experimental tubes.
4. The platelet count (PLT) diminishes with the experimental tubes but stays relatively constant with the control tubes.

TABLE 1

| ACD TUBES | | | | | |
|---|---|---|---|---|---|
| CONTROL | | | | | |
| | 0 | 2 | 4 | 6 | 24 |
| WBC | 6.6 | 6.7 | 6.8 | 6.9 | 6.6 |
| LY | 24.8 | 24.2 | 24.5 | 25.0 | 26.9 |
| MO | 3.7 | 2.1 | 2.4 | 1.8 | 5.7 |
| GR | 71.5 | 73.7 | 73.1 | 73.2 | 67.4 |
| EO | .7 | .7 | .7 | .7 | .7 |
| BA | .2 | .2 | .2 | .2 | .2 |
| RBC | 5.05 | 5.06 | 5.05 | 5.08 | 5.05 |
| HGB | 14.7 | 14.5 | 14.7 | 14.7 | 14.6 |
| HCT | 43.6 | 43.4 | 43.6 | 43.9 | 44.0 |
| MCV | 86.3 | 85.8 | 86.3 | 86.4 | 87.2 |
| MCH | 29.1 | 28.9 | 29.1 | 28.9 | 28.9 |
| MCHC | 33.7 | 33.6 | 33.7 | 33.5 | 33.2 |
| RDW | 13.4 | 13.4 | 13.5 | 13.9 | 14.5 |
| PLT | 299 | 302 | 302 | 302 | 310 |
| MPV | 6.4 | 6.6 | 6.4 | 6.5 | 6.5 |
| EXPERIMENTAL | | | | | |
| | 0 | 2 | 4 | 6 | 24 |
| WBC | 5.9 | 3.2 | 2.4 | 2.0 | 0.4 |
| LY | — | — | — | — | — |
| MO | — | — | — | — | — |
| GR | — | — | — | — | — |
| EO | — | — | — | — | — |
| BA | — | — | — | — | — |
| RBC | 4.81 | 4.68 | 4.83 | 4.81 | 4.77 |
| HGB | 14.2 | 13.8 | 14.1 | 14.1 | 14.0 |
| HCT | 47.5 | 41.5 | 44.6 | 46.0 | 46.7 |
| MCV | 98.8 | 88.6 | 92.4 | 95.7 | 97.8 |
| MCH | 29.5 | 29.5 | 29.2 | 29.3 | 29.4 |
| MCHC | 29.9 | 33.3 | 31.6 | 30.6 | 30.0 |
| RDW | 16.3 | 13.5 | 14.6 | 15.1 | 16.8 |
| PLT | 160 | 173 | 146 | 124 | 106 |
| MPV | 4.4 | 4.3 | 4.3 | 4.2 | 4.6 |

TABLE 2

| EDTA TUBES | | | | | |
|---|---|---|---|---|---|
| CONTROL | | | | | |
| | 0 | 2 | 4 | 6 | 24 |
| WBC | 7.9 | 8.0 | 7.7 | 7.9 | 7.7 |
| LY | 22.8 | 24.0 | 23.2 | 24.1 | 24.6 |
| MO | 5.6 | 4.7 | 4.7 | 5.9 | 25.1 |
| GR | 71.6 | 71.3 | 72.1 | 70.0 | 50.3 |
| EO | .7 | .7 | .7 | .7 | — |
| BA | .2 | .2 | .2 | .2 | — |
| RBC | 5.85 | 5.83 | 5.91 | 5.86 | 5.86 |
| HGB | 17.1 | 16.9 | 17.0 | 16.8 | 16.9 |
| HCT | 50.1 | 50.4 | 50.7 | 50.8 | 51.4 |
| MCV | 85.6 | 86.4 | 85.8 | 86.7 | 87.7 |
| MCH | 29.2 | 29.0 | 28.8 | 28.7 | 28.8 |
| MCHC | 34.1 | 33.6 | 33.5 | 33.1 | 32.9 |
| RDW | 13.3 | 13.4 | 13.4 | 13.7 | 14.7 |
| PLT | 337 | 341 | 341 | 330 | 335 |
| MPV | 7.5 | 7.6 | 7.5 | 7.4 | 7.5 |
| EXPERIMENTAL | | | | | |
| | 0 | 2 | 4 | 6 | 24 |
| WBC | 7.4 | 3.8 | 3.7 | 3.2 | 3.0 |
| LY | 40.5 | — | — | — | — |
| MO | 45.4 | — | — | — | — |
| GR | 14.1 | — | — | — | — |
| EO | — | — | — | — | — |
| BA | — | — | — | — | — |
| RBC | 5.62 | 5.52 | 5.57 | 5.63 | 5.57 |
| HGB | 16.1 | 16.0 | 15.8 | 15.8 | 15.8 |
| HCT | 54.2 | 50.2 | 55.5 | 58.8 | 58.2 |
| MCV | 96.4 | 91.0 | 99.7 | 104.4 | 104.5 |
| MCH | 28.6 | 29.0 | 28.4 | 28.1 | 28.4 |
| MCHC | 29.7 | 31.9 | 28.5 | 26.9 | 27.1 |
| RDW | 16.0 | 13.9 | 19.4 | 25.1 | 18.0 |
| PLT | 331 | 332 | 293 | 309 | 239 |
| MPV | 8.9 | 7.9 | 7.4 | 7.5 | 7.3 |

EXAMPLE 2

Substantially similar tests as in Example 1 were run with several other commercially available detergents with the results as set for in Table 3 as follows:

TABLE 3

| Detergents that work same as BRIJ 35 (good): | |
|---|---|
| 1. TEEPOL HB7 | WBC count goes down |
| | RBC count is steady |
| | Platelets and MCV are OK |
| 6. BRIJ 58 | WBC count goes down |
| | RBC count is steady |
| | MCV and Platelet value is OK |
| 7. POLYOXYETHYLENE ETHER 20 STEARYL ETHER | |
| | WBC count goes down |
| | RBC count is steady |
| | MCV changes are OK |
| | Platelet values are steady |
| Detergents that do not work the same as BRIJ 35 (no good): | |
| 2. TERGITOL NP-7 | WBC count does not change |
| | RBC count goes down |
| | MCV and Platelet change with time |
| 3. BRIJ 30 | WBC count does not change |
| | Some RBC lysis |
| | MCV goes very high |
| 4. BRIJ 96 | WBC count does not change |
| | RBC lysis |
| | MCV value is too low |
| 5. TWEEN 20 | WBC count does not change |
| | RBC count stays the same |
| | MCV value is steady |
| | Platelet count diminishes |

Various other examples will be apparent to the person skilled in the art without departing from the spirit and scope of the invention. It is intended that all such other examples be included within the scope of the appended claims.

What is claimed is:

1. A method for removing intracellular virus from white blood cells which comprises treating said white blood cells in vitro at a temperature of from about 2° C. to about 45° C. with an effective amount of about 0.2% to about 50% by volume of a special detergent which selectively lyses said white blood cells without causing substantial lyses of any red blood cells in admixture therewith to thereby release the white blood cell-contained virus into the cell medium or cell lysate, in which said special detergent is a polyethylene glycol fatty alcohol ether which contains from about 20 to 23 oxyethylene groups in the molecule and is a derivative of a $C_{12}$–$C_{18}$ fatty alcohol.

2. The method of claim 1 in which the special detergent is polyoxyethylene (23) lauryl ether.

3. The method of claim 1 in which the active detergent concentration is ca. 1–2% by volume of the treated white blood cell mixture.

4. The method of claim 1 in which the special detergent is added to blood or blood cell packs to cause said lyses followed by removal of the lysed material prior to administration of the thus treated blood or blood cell packs.

5. The method of claim 3 in which the special detergent is polyoxyethylene (23) lauryl ether.

6. The method of claim 4 in which the special detergent is polyoxyethylene (23) lauryl ether.

7. The method of claim 6 in which the active detergent concentration is ca. 1–2% by volume of the treated white blood cell mixture.

* * * * *